United States Patent [19]

Weber et al.

[11] 4,311,854

[45] Jan. 19, 1982

[54] PROCESS FOR THE PRODUCTION OF DI-N-PROPYL-ACETIC ACID

[75] Inventors: Jürgen Weber, Oberhausen; Volker Falk, Voerde; Claus Kniep, Oberhausen, all of Fed. Rep. of Germany

[73] Assignee: Ruhrchemie Aktiengesellschaft, Oberhausen, Fed. Rep. of Germany

[21] Appl. No.: 60,560

[22] Filed: Jul. 25, 1979

[30] Foreign Application Priority Data

Oct. 13, 1978 [DE] Fed. Rep. of Germany ....... 2844638

[51] Int. Cl.$^3$ .................. C07C 51/235; C07C 53/128
[52] U.S. Cl. .................................... 562/531; 562/606; 568/397; 568/451; 568/881; 585/640
[58] Field of Search ............................... 562/531, 606; 260/604 HF, 595; 585/640; 568/397, 451, 881

[56] References Cited

U.S. PATENT DOCUMENTS 4,127,604 11/1978 Chignac ............................ 562/606

FOREIGN PATENT DOCUMENTS 7605350 11/1976 U.S.S.R. ............................ 562/606

*Primary Examiner*—Vivian Garner

*Attorney, Agent, or Firm*—Sprung, Felfe, Horn, Lynch & Kramer

[57] ABSTRACT

A process for the preparation of di-n-propyl-acetic acid, comprising the steps of:
  A. catalytically reacting n-butyric acid with cleavage of carbon dioxide and water to form heptanone-4;
  B. hydrogenating heptanone-4 in teh presence of a catalyst to form heptanol-4;
  C. dehydrating heptanol-4 in the presence of an Al$_2$O$_3$ catalyst to form heptene-3;
  D. hydroformylating heptene-3 in the presence of a rhodium complex compound as catalyst to form a mixture of 2-propyl pentanal and 2-ethyl hexanal;
  E. oxidizing the 2-propyl pentanal/2-ethyl hexanal mixture to form a mixture of di-n-propyl acetic acid and 2-ethyl hexanoic acid, and
  F. separating the mixture of di-n-propyl acetic acid and 2-ethyl hexanoic acid to recover pure di-n-propyl acetic acid.

If desired, step B can be carried out without purification of the product of step A. Moreover, the dehydration of step C can be carried out without previous purification of the product of step B. Step D can also be carried out without purification of the product of step C.

13 Claims, No Drawings

PROCESS FOR THE PRODUCTION OF DI-N-PROPYL-ACETIC ACID

BACKGROUND OF THE INVENTION

1. Field of the Invention

The invention relates to a new process for the production of di-n-propyl-acetic acid from n-butyric acid.

2. Discussion of the Prior Art

Derivatives of di-n-propyl-acetic acid have gained great importance as psychopharmacologic drugs and antiepileptics. Several syntheses for the preparation of the acid have already been described.

In a known process, the starting material is malonic acid diethyl ester which is reacted initially with sodium methylate and then with allyl chloride to form d-allyl-diethyl malonate. Saponification with sodium hydroxide gives the sodium salt of diallyl malonic acid which is thermally decarboxylated to form diallyl acetic acid and subsequently hydrogenated partially to form di-n-propyl-acetic acid. The process requires the use of expensive starting materials which are difficult to handle technically such as sodium methylate and allyl chloride.

Another mode of operation varies a process for the preparation of di-isopropylacetic acid having been described by Sarel, J. Am. Chem. Soc. 78, 5416-5420 (1956). In this process, cyanoacetic acid ester is alkylated in the presence of sodium isopropylate by means of isopropyl iodide. This results in the formation of diisopropyl-cyanoacetic acid ester which is decarboxylated to form diisopropylacetonitrile. In further steps, the diisopropylacetonitrile is converted into diisopropylacetic acid via diisopropylacetic acid amide. The application of this reaction route to the synthesis of di-n-propylacetic acid results, however, in total yields of only 10 to 40% and, therefore, is commercially unattractive.

East German (DDR) Patent No. 129,776 describes a process for the production of di-n-propylacetic acid which starts from an ester of cyanoacetic acid. Reaction with n-propyl bromide or iodide in the presence of sodium-n-propylate, saponification of the di-n-propyl-cyanoacetic acid ester by means of caustic and acidification result in 2,2-di-n-propylcyanoacetic acid which is decarboxylated to form di-n-propylacetonitrile. The acetonitrile is subsequently converted with aqueous sulfuric acid via the acetamide into di-n-propyl-acetic acid. This process also uses expensive starting materials and requires the use of reaction steps which cannot be carried out continuously. Moreover, since the hydrolysis of acetamide to form the acid is carried out in the presence of sodium nitrite, problems in connection with environmental pollution are encountered.

It is, therefore, an object of this invention to provide a process for the preparation of di-n-propylacetic acid which starts from inexpensive starting materials which are available in commercial amounts at moderate prices, comprises reaction steps which are readily carried out commercially and synthesizes the desired product available in satisfactory yields.

These requirements are surprisingly met by a process for the preparation of di-n-propyl-acetic acid, which comprises the steps of:

A. catalytically reacting n-butyric acid to form heptanone-4 with cleavage of carbon dioxide and water;
B. hydrogenating heptanone-4 in the presence of a catalyst to form heptanol-4;
C. dehydrating heptanol-4 in the presence of an $Al_2O_3$ catalyst to form heptene-3;
D. hydroformylating heptene-3 in the presence of a rhodium complex compound as catalyst to form a mixture of 2-propyl pentanal and 2-ethyl hexanal;
E. oxidizing the 2-propyl pentanal/2-ethyl hexanal mixture to form a mixture of di-n-propyl-acetic acid and 2-ethyl hexanoic acid, and
F. separating the mixture of di-n-propyl-acetic acid and 2-ethyl hexanoic acid to recover pure di-n-propyl-acetic acid.

The preparation of ketones from carboxylic acids is a known reaction. In this reaction, 1 molecule of ketone is formed from 2 molecules of an acid with cleavage of carbon dioxide and water. The reaction is usually carried out at temperatures between 300° and 600° C. in the presence of catalysts such as chromium oxide, iron, thorium dioxide and manganese (IV) oxide (see, for example, Methodicum Chemicum, Vol. 5, page 462). The reaction is carried out with a space velocity of 0.25 cu.m/hr.cu.m.

The use of $ThO_2/Al_2O_3$ catalysts has been described specifically for the preparation of heptanone-4 from butyric acid (see, for example, Italian Patent 660 9 10). Since thorium is radioactive, narrow limits are set to the use of catalysts of this kind in industry.

It has been found that the reaction of n-butyric acid to heptanone-4 takes place with particularly good success at 350° to 450° C. in the presence of catalysts which contain lanthanum, e.g., in an amount of 0.2 to 20 weight percent. While values of 70% are generally reported for the selectivity of the ketone formation, it is approximately 100% when using lanthanum catalysts. Thus, n-butyric acid is converted over a catalyst composed of 2% by weight of lanthanum (as $La_2O_3$), the balance being $Al_2O_3$, into heptanone-4 with a selectivity of >99% at a conversion of about 92%.

In the reaction step which follows, the heptanone-4 is hydrogenated to form the corresponding alcohol, i.e., heptanol-4, whithout previous purification being necessary. The reaction with hydrogen is carried out in the liquid phase in the presence of catalysts at temperatures which are dependent on the kind of the hydrogenation catalyst used. Particularly favorable results are obtained with nickel catalysts which contain 30 to 70% by weight of nickel (based on total catalyst) in addition to a support such as alumina, $SiO_2$, artificial or natural silicates. Preferred is a catalyst which contains 50 to 60% of nickel in addition to kieselguhr as the support. It requires a reaction temperature of 100° to 200° C. A hydrogen pressure of 80 to 150 bars is suitable. The reaction is performed generally up to 4 hours. With a quantitative conversion of the starting material, heptanol-4 is obtained with a selectivity of 97% and more.

After separation of the hydrogenation catalyst, the alcohol can be subjected to the dehydration reaction directly, i.e., again without previous purification. However, it is desirable in several cases to subject the alcohol previously to a coarse distillation so that it is present in a purity of more than 98%. Dehydration of heptanol-4 to heptanone-3 is carried out in the gaseous phase at temperatures between 200° and 350° C. in the presence of an $Al_2O_3$ catalyst in which the alumina is preferably present in the γ-modification. Catalysts which contain about 3% of carbon, e.g., in the form of graphite, and ≦0.01% of $Na_2O$ or $K_2O$, ≦0.01% of iron oxide and ≦0.01% of silica in addition to alumina are used with particular success.

Surprisingly, the dehydration of heptanol takes place in the presence of such catalysts without the formation of isomerization products which are produced to a considerable extent if other catalysts are used. A conversion of more than 95% is achieved at temperatures of 250° to 350° C. and a space velocity of 0.2 to 0.8 cu. m./hr.cu.m. The selectivity for heptene-3 formation is 99%.

The heptene-3 obtained by dehydration of heptanol-4 can be subjected directly to the hydroformylation without previous processing or purification. The reaction is carried out as usual in the presence of carbonyl-forming metals of Group 8 of the Periodic Table. The use of rhodium as catalyst which is contained in the reaction mixture in the form of a rhodium complex which contains phosphine has been found to be particularly advantageous. In practice, heptene, a rhodium salt, e.g., rhodium chloride or rhodium hexanoate, and an aliphatic or aromatic phosphine are charged to a pressure vessel. Examples of suitable phosphines include triphenyl phosphine and especially tributyl phosphine. The molar ratio of rhodium salt to phosphine ranges between 1:50 and 1:150 and the Rh concentration, based on the total reaction mixture, between 10 and 100 ppm. Carbon monoxide and hydrogen are desirably introduced into the reactor in a ratio of 1:1. The reaction takes place at 100° to 180° C. and a pressure of 150 to 300 bars. The carbon monoxide-hydrogen mixture is introduced into the reactor so that the reaction pressure chosen is maintained. The use of rhodium catalysts containing a phosphine as complex ligand has the unexpected result that the olefin is reacted quantitatively to a mixture of 70 to 75% by weight of 2-propyl pentanal and 25 to 30% by weight of 2-ethyl hexanal. By-products by isomerization of the starting olefin are not produced.

The hydroformylation product is processed in known manner by separation of the catalyst and distillation. There results a mixture of about 75% by weight of 2-propyl pentanal and 25% by weight of 2-ethyl hexanal, which contains contaminations only to a minor extent.

This aldehyde mixture is oxidized with oxygen at 20° to 80° C. A molecular oxygen-containing gas is suitable for the oxidation which will be carried out without pressure. Alkali metal salts of higher fatty acids, i.e., monocarboxylic acids having 3 to 12 carbon atoms, e.g., Na-2-ethyl hexanoate, are added as catalyst in an amount of 0.2 to 1.5% by weight, based on the weight of the total reaction mixture. The use of sodium salts as catalysts has the advantage that the reaction proceeds at low temperatures, i.e., in a range of 25° to 35° C., with high selectivity. To obtain pure di-n-propyl acetic acid, separation of the mixture consisting of 2-propyl pentanal and 2-ethyl hexanal by distillation under vacuum has been found to be advantageous. It is desirable to use a column having at least 60 theoretical plates at a reflux ratio of at least 5:1. At pressures of 20 to 50 bars, di-n-propyl acetic acid boils at temperatures between 133° and 154° C.

The process according to the invention is illustrated in greater detail in the example which follows.

EXAMPLE

Step 1: Preparation of heptanone-4

A quartz tube of 120 cm length and 28 mm inside diameter is filled with 300 ml of catalyst corresponding to a bed height of about 80 cm. The catalyst consists of 2% by weight of lanthanum in the form of di-lanthanum trioxide on alumina balls of the Péchiney A type (2 to 4 mm diameter). A layer of 30 cm of Raschig rings (4 mm diameter) functioning as evaporation zone is arranged above the catalyst. The tube is heated to the necessary temperature of 350° C. in an electric furnace. An intense condenser terminating in a receiver with drain valve is connected at the lower outlet of the reactor. After a temperature of 350° C. has been reached, n-butyric acid is introduced at the top of the reaction tube at a controlled rate. At the same time, the temperature is increased to 450° C. Thereby the starting product evaporates in the Raschig ring zone. It contacts in gaseous form the catalyst bed and is reacted with cleavage of water and $CO_2$ to form the corresponding ketone. After having emerged from the reactor, the vapor condenses in the intense condenser arranged downstream of the reactor. The resultant liquid product is collected in a receiver.

The reaction product is obtained at a rate of 75 ml per hour corresponding to a space velocity of 0.25. The organic phase and the aqueous phase are separated. The conversion is 92% and the selectivity (based on heptanone-4) >99%. The heptanone-4 is obtained in a purity of 99%.

Characteristics of the product:
Boiling point 145° C.
Refractive index at 20° C.: $n_D^{20} = 1.4070$.
Density at 20° C.: $D_4^{20} = 0.817$.

Step 2: Preparation of heptanol-4

The catalytic hydrogenation of heptanone-4 is carried out in the presence of a nickel catalyst which contains 55% of Ni on kieselguhr.

600 ml of the ketone and 30 ml of catalyst are charged to a 2.8 liter autoclave. The starting material is reacted quantitatively within about 3 hours at 150° C. and 100 bars. According to the analysis by gas chromatography, the reaction product contains 97% of heptanol-4, the balance consisting of unreacted ketone. Distillation gives 537 g (88% of the theory) of heptanol-4 having a purity of 99.9%.

Characteristics of the product:
Boiling point 156° C.
Refractive index at 20° C.: $n_D^{20} = 1.4190$.
Density at 20° C. $D_4^{20} = 0.818$.

Step 3: Preparation of heptene-3

$\gamma$-$Al_2O_3$ is used as catalyst (0423 T, produced by Chemische Werke Huels AG) for the dehydration of heptanol-4. The tube described for step 1 with the associated accessories is used as reaction vessel. The tube is filled with 300 ml of catalyst in the form of tablets (diameter, 4 mm) and heated to 270° to 280° C. The optimum residence time is reached at a space velocity V/V/h of 0.5 ($\hat{=}$150 ml throughput per hour). Under these conditions which are relatively mild for a dehydration, the conversion is >95% while the selectivity for heptene-3 is 99%.

The reaction product requires no additional purification for the further use. Yield, 94% of the theory.

Characteristics of the product:
Boiling point: 96° C.
Refractive index at 20° C.: $n_D^{20} = 1.4051$.
Density at 20° C.: $D_4^{20} = 0.700$.

Step 4: Preparation of 2-propyl-pentanal

Into an autoclave are charged 294.6 g (≙420 ml, 3 moles) of heptene-3, 50 ppm of Rh (based on heptene-3) in the form of $RhCl_3$, and 2.8 g of tributyl phosphine (molar ratio of Rh:phosphine=1:100). A pressure of 150 bars is adjusted by introducing CO and $H_2$ (molar ratio, 1:1). Thereafter, the temperature is increased to 130° C. and the pressure to 290 bars. After 3 hours, the olefin is reacted quantitatively. As is shown by the analysis by gas chromatography, the reaction product contains 2-propyl pentanal and 2-ethyl hexanal in a ratio of about 75:25. The yield (2-propyl pentanal + 2-ethyl hexanal) is 346 g. The hydroformylation product is directly oxidized after flash distillation.

Step 5: Preparation of 2-propyl-pentanoic acid (di-n-propyl-acetic acid)

420 grams of hydroformylation product as obtained by the process of step 4 and 4.2 g of freshly prepared Na-2-propyl-pentanoate are charged to a bubble column reactor and treated with oxygen at 30° C. After 4 hours, the conversion is already 94.5%, complete conversion requiring a reaction time of 7 hours.

According to the analysis by gas chromatography, the reaction product contains about 90% of the mixture of 2-propyl-pentanoic acid and 2-ethyl-hexanoic acid. Distillation in a column having 90 theoretical plates at a reflux ratio of 10:1 under a pressure of 20 Torr gives 2-propyl-pentanoic acid having a purity of 99.1%. The yield of 2-propyl-pentanoic acid is 238 g.

Characteristics of the product:
Boiling point: 118° C./10 mm Hg.
Refractive index at 20° C.: $n_D^{20} = 1.4249$.
Density at 20° C.: $D_4^{20} = 0.905$.

Additionally, about 100 g of 99.2% 2-ethyl-hexanoic acid are recovered as the second fraction.

We claim:

1. A process for the preparation of di-n-propylacetic acid comprising the steps of:
   A. catalytically reacting n-butyric acid with cleavage of carbon dioxide and water to form heptanone-4 by heating said n-butyric acid at a temperature of 300° to 600° C. in the presence of a catalyst selected from the group consisting of chromium oxide, iron, lanthanum, thorium dioxide and manganese (IV) oxide;
   B. hydrogenating heptanone-4 in the presence of a catalyst to form heptanol-4, the hydrogenation being carried out in the liquid phase at a reaction temperature of 100° to 200° C. employing a hydrogen pressure of 80 to 150 bars;
   C. dehydrating heptanol-4 in the presence of an $Al_2O_3$ catalyst to form heptene-3, the dehydration being carried out in the gaseous phase at a temperature between 200° and 350° C.;
   D. hydroformylating heptene-3 in the presence of a rhodium complex compound as catalyst to form a mixture of 2-propyl pentanal and 2-ethyl hexanal;
   E. oxidizing the 2-propyl pentanal/2-ethyl hexanal mixture by contacting the same at 20° to 80° C. with oxygen in the presence of an alkali metal salt of a higher monocarboxylic acid as catalyst to form a mixture of di-n-propyl acetic acid and 2-ethyl hexanoic acid and
   F. separating the mixture of di-n-propyl acetic acid and 2-ethyl hexanoic acid to recover pure di-n-propyl acetic acid.

2. Process according to claim 1 wherein the formation of heptanone-4 from butyric acid is carried out at a temperature of 350° C. to 450° C. in the presence of a supported catalyst containing lanthanum.

3. Process according to claim 2 wherein $Al_2O_3$ is used as the support for the lanthanum-containing catalyst.

4. Process according to claim 1 wherein the heptanone-4 is hydrogenated in the presence of a supported catalyst containing 50 to 60% of nickel to form heptanol-4

5. Process according to claim 1 wherein the dehydration of heptanol-4 to form heptene-3 is carried out at a temperature of 250° to 350° C.

6. Process according to claim 1 wherein the dehydration of heptanol-4 to form heptene-3 is carried out in the presence of a catalyst which contains about 3% of carbon in addition to $\gamma$-$Al_2O_3$.

7. Process according to claim 1 wherein the hydroformylation of heptene-3 is carried out at 100° to 180° C. and 150 to 300 bars in the presence of a rhodium catalyst which contains phosphine as complex ligand.

8. Process according to claim 1 wherein the rhodium catalyst contains tributyl phosphine as complex ligand and the molar ratio of rhodium to phosphine is 1:150.

9. Process according to claim 1 wherein step B is carried out without any purification of the product of step A.

10. Process according to claim 1 wherein step C is carried out without any previous purification of the product of step B.

11. Process according to claim 1 wherein step D is carried out without any previous purification of the product of step C.

12. Process according to claim 1 wherein steps B, C and D are each carried out without any previous purification of the product of any preceding step.

13. A process for the preparation of di-n-propyl acetic acid comprising the steps of:
   (a) contacting n-butyric acid with a catalyst selected from the group consisting of chromium oxide, iron, thorium dioxide, lanthanum, and manganese (IV) oxide at a temperature between 300° and 600° C. to form heptanone-4 with cleavage of carbon dioxide and water;
   (b) contacting said heptanone-4 with hydrogen at a temperature of 100° to 200° C. in the liquid phase at a hydrogen pressure of 80 to 150 bars in the presence of a catalyst to form heptanol-4;
   (c) dehydrating said heptanol-4 by contacting the same in the gas phase at a temperature of 200° to 350° C. with an $Al_2O_3$ catalyst to form heptene-3;
   (d) hydroformylating heptene-3 in the presence of a rhodium complex compound as catalyst to form a mixture of 2-propyl pentanal and 2-ethyl hexanal;
   (e) oxidizing the 2-propyl pentanal/2-ethyl hexanal mixture by contacting the same with a molecular oxygen containing gas at 20° to 80° C. to form a mixture of di-n-propylacetic acid and 2-ethyl hexanoic acid and
   (f) separating the mixture of di-n-propylacetic acid and 2-ethyl hexanoic acid to recover pure di-n-propylacetic acid.